(12) United States Patent
Jamieson et al.

(10) Patent No.: US 7,622,255 B2
(45) Date of Patent: Nov. 24, 2009

(54) METHODS OF IDENTIFYING AND ISOLATING STEM CELLS AND CANCER STEM CELLS

(75) Inventors: Catriona Helen M. Jamieson, La Jolla, CA (US); Laurie Ailles, Palo Alto, CA (US); Tannishtha Reya, Chapel Hill, NC (US); Irving L. Weissman, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/799,817

(22) Filed: May 2, 2007

(65) Prior Publication Data

US 2007/0238127 A1    Oct. 11, 2007

Related U.S. Application Data

(63) Continuation of application No. 10/449,795, filed on May 30, 2003, now Pat. No. 7,217,568.

(60) Provisional application No. 60/431,655, filed on Dec. 6, 2002, provisional application No. 60/384,529, filed on May 31, 2002.

(51) Int. Cl.
C12Q 1/68 (2006.01)
C12Q 1/02 (2006.01)
C12N 15/00 (2006.01)

(52) U.S. Cl. .............................. 435/6; 435/29; 435/455

(58) Field of Classification Search .................... 435/6, 435/29, 455
See application file for complete search history.

(56) References Cited

U.S. PATENT DOCUMENTS

| | | | |
|---|---|---|---|
| 5,652,122 | A | 7/1997 | Frankel et al. |
| 5,851,984 | A | 12/1998 | Matthews et al. |
| 6,465,249 | B2 | 10/2002 | Reya et al. |
| 2002/0004241 | A1 | 1/2002 | Reya et al. |
| 2003/0064384 | A1 | 4/2003 | Hung et al. |

FOREIGN PATENT DOCUMENTS

WO    WO01/52649 A1    7/2001

OTHER PUBLICATIONS

Tsutsui J., Expression of Cadherin-catenin complexes in human leukemia cell lines, 1996, J. Biochem., vol. 120, pp. 1034-1039.*
Soligo D., The apoptotic response to human myeloid leukaemia cell lines and of normal and malignant haematoietic progenitor cells to the proteasome inhibitor PSI, 2001, British J. of Haematology, vol. 113, pp. 126-135.*
2008, Hu et al., Leukemia, Nature Publishing, Adv. Publication, pp. 1-8.*
Aberle et al., "β-catenin is a target for the ubiquitin-proteasome pathway," EMBO J, 1997, 16(13):3797-3804.
Arnold et al., "Brachyury is a target gnee of the WntJBeta-catenin signaling pathway," Mech. Dev., 2000, 91(1-2):249-258.
Chu et al., "Retrovirus-Mediated Gene Transfer into Human Hematopoietic Stem Cells," J Mol. Med., 1998, 76 (3-4):184-192.
Damalas et al., "Excess β-Catenin Promotes Accumulation of Transcriptionally Active p53," EMBO J, 1999, 18 (11):3054-3063.
DasGupta et al., "Multiple roles for activated LEF/TCF transcription complexes during hair follicle development and differentiation," Development, 126(20):4557-4568.
Domen et al., "Self-renewal, differentiation or death: regulation and manipulation of hematopoietic stem cell fate," Mol. Med. Today, 1999, 5(5):201-208.
Follenzi et al., "Gene transfer by lentiviral vectors is limited by nuclear translocation and rescued by HIV-1 pol sequences," Nat. Genet., 2000, 25(2):217-222.
He et al., "Identification o f c-MYC as a Target of the APC Pathway," Science, 1998, 281(5382):1509-1512.
Hinck et al., "Wnt-1 Modulates Cell-Cell Adhesion in Mammalian Cells by Stabilizing β-Catenin Binding to the Cell Adhesion Protein Cadherin," J Cell Biol., 1994, 124(5):729-741.
Huelsken et al., "New aspects of Wnt signaling pathways in higher vertebrates," Curr. Opin. Genet. Dev., 2001, 11 (5):547-553.
Kielman et al., "Apc modulates embryonic stem-cell differentiation by controlling the dosage of beta-catenin signaling,", Nat. Genet., 2002, 32(4):594-605.
Korinek et al., "Depletion of epithelial stem-cell compartments in the small intestine of mice lacking Tcf-4," Nat. Genet., 1998, 19(4):379-383.
Korinek et al., "Constitutive Transcriptional Activation by a β-Catenin-Tcf Complex in APC-/- Colon Carcinoma," Science, 1997, 275(5307):1784-1787.
Miyoshi et al., "Activation of the β-Catenin Gene in Primary Hepatocellular Carcinomas by Somatic Alterations Involving Exon 3," Cancer Res., 1998, 58(12)2524-2527.
Morin et al., "Activation of β-Catenin-Tcf Signaling in Colon Cancer by Mutations in β-Catenin or APC," Science, 1997, 275(5307):1787-1790.
Müller et al., "A β-catenin Mutation in a Sporadic Colorectal Tumor of the RER Phenotype and Absence of β-catenin Germline Mutations in FAP Patients," Genes Chromosomes Cancer, 1998, 22(1):37-41.

(Continued)

Primary Examiner—Valarie Bertoglio
Assistant Examiner—David Montanari
(74) Attorney, Agent, or Firm—Bozicevic Field & Francis LLP; Pamela J. Sherwood

(57) ABSTRACT

Methods and compositions are provided for the identification of stem cells and cancer stem cells. β-catenin is also identified as a target for the development of therapeutic moieties against hematopoietic tumors, i.e. leukemia and lymphoma cells, which may include screening assays directed at β-catenin, or members of the β-catenin signaling pathway. Cellular proliferation in hematopoietic cells can be altered by introducing stabilized β-catenin into a hematopoietic cell that is altered in its ability to undergo apoptosis but which is not fully transformed. The immortalized cells are useful in screening assays, and in the analysis of pathways by which hematopoietic cells undergo transformation.

9 Claims, 8 Drawing Sheets

OTHER PUBLICATIONS

Palacios et al., "Mutations in the β-catenin Gene (CTNNB1) in Endometrioid Ovarian Carcinomas," Cancer Res., 1998, 58(7):1344-1347.

Plescia et al., "Genomic expression analysis implicates Wnt signaling pathway and extracellular matrix alterations in hepatic specification and differentiation of murine hepatic stem cells," Differentiation, 2001, 68(4-5):254-269.

Reya et al., "Stem cells, cancer, and cancer stem cells," Nature, 2001, 414(6859):105-111.

Roose et al., "TCF transcription factors: molecular switches in carcinogenesis," Biochim. Biophys. Acta, 1999, 1424 (2-3):M23-M37.

Satoh et al., "Successful Transfer of ADA Gene in vitro into Human Peripheral Blood CD34+ Cells by Transfecting EBV-Based Episomal Vectors," FEBS Lett., 1998, 441(1):39-42.

Shtutman et al., "The cyclin D1 gene is a target of the β-catenin/LEF-1 pathway," Proc Natl Acad Sci USA, 1999, 96(10):5522-5527.

Song et al., "Wingless signaling regulates the maintenance of ovarian somatic stem cells in Drosophila," Development, 2003, 130(14):3259-3268.

Voeller et al. "β-Catenin Mutations in Human Prostate Cancer," Cancer Res., 1998, 58(12):2520-2523.

Wong et al., "Selection of multipotent stem cells during morphogenesis of small intestinal crypts of Lieberkuhn is perturbed by stimulation of Lef-1/beta-catenin signaling," J Biol. Chem., 2002, 277(18):15843-15850.

Xu et al., "WISP-1 is a Wnt-1- and beta-catenin-responsive oncogene," Genes Dev., 2000, 14(5):585-595.

Yang et al., "The sub-cellular distribution of beta-catenin in the neural differentiation of RA induced P19 EC cells," Sheng Li Xue Bao: Acta Physiologica Sinica, National Library of Medicine, 1998, 50(6):671-678.

Young et al., "Wnt-1 Induces Growth, Cytosolic β-Catenin, and Tcf/Lef Transcriptional Activation in Rat-1 Fibroblasts," Mol. Cell. Biol., 1998, 18(5):2474-248.

Zarrin et al., "Comparison of CMV, RSV, SV40 Viral and Vlambda1 Cellular Promoters in B and T Lymphoid and Non-Lymphoid Cell Lines," Biochim. Biophys. Acta, 1999, 1446(1-2):135-139.

Zhou, "Fluorescence-based functional assay for Wnt/beta-catenin signaling activity," Biotechniques, 2002, 33 (5):1126-1128, 1130, 1132 passim.

Zhu et al., "β-catenin signalling modulates proliferative potential of human epidermal keratinocytes independently of intercellular adhesion," Development, 1999, 126(10):2285-2298.

Ziegler et al., "Expansion of stem and progenitor cells," Curr. Opin. Hematol., 1998, 5(6):434-440.

Zurawel et al., "Sporadic Medulloblastomas Contain Oncogenic β-Catenin Mutations," Cancer Res., 1998, 58 (5):896-899.

DasGupta et al., "Multiple roles for activated LEF/TCF transcription complexes during hair follicle development and differentiation," Development, 126(20):4557-4568, Oct. 1999.

* cited by examiner

FIGURE 4
Normal Control
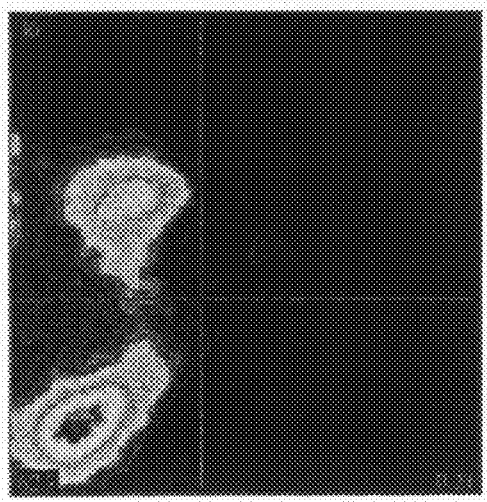
Human Bcl-2 FITC
B-catenin Transplant
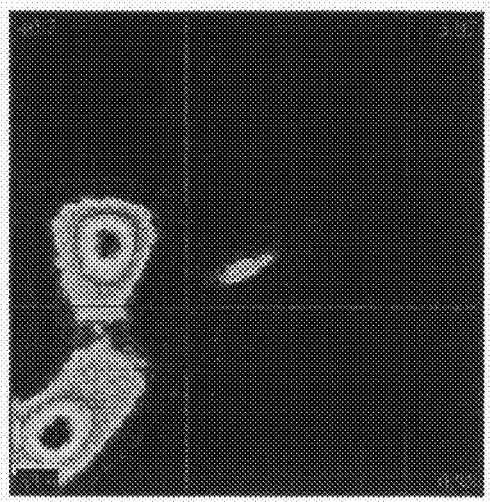
Human Bcl-2 TC

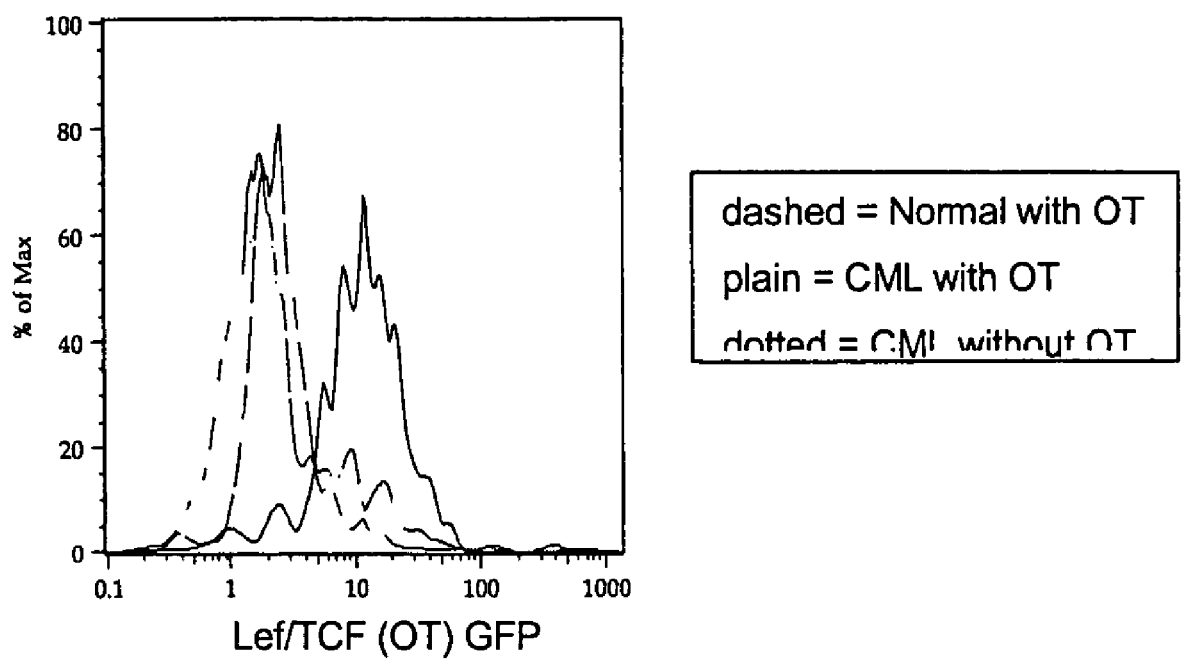

METHODS OF IDENTIFYING AND ISOLATING STEM CELLS AND CANCER STEM CELLS

FEDERALLY-SPONSORED RESEARCH OR DEVELOPMENT

This invention was made with Government support under contract CA086017 awarded by the National Institutes of Health. The Government has certain rights in this invention.

BACKGROUND OF THE INVENTION

Basic cancer research has focused on identifying the genetic changes that lead to cancer. This has led to major advances in understanding of the molecular and biochemical pathways that are involved in tumorigenesis and malignant transformation. But understanding of the cellular biology has lagged. While the effect of particular mutations on the proliferation and survival of model cells may be known, it is not known what the effects of such mutations will be on the actual cells involved in particular cancers.

In fact, many observations suggest that analogies between normal stem cells and tumorigenic cells may be appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials. Because most tumors have a clonal origin, tumorigenic cancer cells must give rise to phenotypically diverse progeny, including cancer cells with indefinite proliferative potential, as well as cancer cells with limited or no proliferative potential. This suggests that tumorigenic cancer cells undergo processes that are analogous to the self-renewal and differentiation of normal stem cells. It is well documented that many types of tumors contain cancer cells with heterogeneous phenotypes reflecting aspects of the differentiation that normally occurs in the tissues from which the tumors arise. The variable expression of normal differentiation markers by cancer cells in a tumor suggests that some of the heterogeneity in tumors arises as a result of the anomalous differentiation of tumor cells. Thus, tumorigenic cells can be thought of as cancer stem cells that undergo an aberrant and poorly regulated process of organogenesis analogous to that of normal stem cells.

Many pathways that are classically associated with cancer may also regulate normal stem cell development. For example, the prevention of apoptosis by enforced expression of the oncogene bcl-2 results in increased numbers of hematopoietic stem cells (HSC) in vivo, suggesting that cell death has a role in regulating the homeostasis of HSCs. Other signaling pathways associated with oncogenesis, such as the Notch, Sonic hedgehog (Shh) and Wnt signalling pathways, may also regulate stem cell self-renewal. One particularly interesting pathway that has also been shown to regulate both self-renewal and oncogenesis in different organs is the Wnt signalling pathway.

It has been suggested that stem cells themselves the target of transformation in certain types of cancer. Because stem cells have the machinery for self-renewal already activated, maintaining this activation may be simpler than turning it on de novo in a more differentiated cell. Also, by self-renewing, stem cells often persist for long periods of time, instead of dying after short periods of time like many mature cells in highly proliferative tissues. This means that there is a much greater opportunity for mutations to accumulate in individual stem cells than in most mature cell types. Restricted progenitors could potentially be transformed either by acquiring mutations that cause them to self-renew like stem cells, or by inheriting existing mutations from stem cells, such that only a single mutation is required in the progenitors to cause transformation.

Although stem cells are often the target of genetic events that are necessary or sufficient for malignant transformation, in other cases restricted progenitors or even differentiated cells may become transformed. In the case of spontaneously arising human leukemias it is likely that stem cells accumulate the mutations that are necessary for neoplastic proliferation; however, these mutations may accumulate in stem cells even while the effects of the mutations are expressed in restricted progenitors. That is, mutations that accumulate in stem cells may lead to neoplastic proliferation of primitive progenitors downstream of stem cells.

Methods of identifying and isolating stem cells and cancer stem cells are of great interest for the understanding of mechanisms that govern these cells, and for the development of therapeutic modalities that can be appropriately targeted for the treatment of cancers and modulation of stem cell growth and development.

SUMMARY OF THE INVENTION

Methods and compositions are provided for the identification of stem cells and cancer stem cells. To detect the cells of interest, a nucleic acid construct is introduced into a cell or population of cells, where the construct comprises sequences encoding a detectable marker, which marker is operably linked to a transcriptional response element regulated by β-catenin. In the presence of active, nuclear β-catenin, the detectable marker is expressed, and indicates that a cell is a stem cell. In this aspect, the method may be used to determine whether a test cell, particularly a normal, or non-transformed cell, is a stem cell. In some embodiments of the invention, the detectable marker is a fluorescent protein, e.g. green fluorescent protein (GFP) and variants thereof. Viable cells expressing GFP can be sorted, in order to isolate or enrich for the stem cells of interest. In this aspect, the methods may be used to enrich for known stem cells and to select for previously unknown stem cells.

In some embodiments of the invention, the population of cells is a mixed population of stem cells and non-stem cells, e.g. committed progenitor cells, differentiated cells, etc. Stem cells, for these purposes, may include normal stem cells, such as hematopoietic stem cells, embryonic stem cells, neural stem cells, and the like, or may be tumor stem cells. Populations of cells may include tumors, e.g. solid tumors, blood samples from leukemia patients, and the like, as well as populations of normal cells, e.g. bone marrow, epithelial tissue, and the like.

In another embodiment of the invention, β-catenin is identified as a target for the development of therapeutic moieties against hematopoietic tumors, i.e. leukemia and lymphoma cells and against tumor stem cells. Methods may include screening assays directed at β-catenin, or members of the β-catenin signaling pathway. Such hematopoietic tumors are also characterized and diagnosed according to the presence of abnormal β-catenin, e.g. inappropriate nuclear translocation, over-expression, and the like.

In another embodiment of the invention, methods are provided for the alteration of cellular proliferation in hematopoietic cells, by introducing stabilized β-catenin into a hematopoietic cell that is altered in its ability to undergo apoptosis but which is not fully transformed, i.e. capable of forming tumors in serial transplant. The immortalized cells are useful in screening assays, and in the analysis of pathways by which hematopoietic cells undergo transformation.

BRIEF DESCRIPTION OF THE DRAWINGS

FIG. 4 is a comparison of normal and β-catenin transplanted cells.

FIG. 7 depicts the increased expression of a marker gene under control of a β-catenin responsive element in CML progenitor cells (granulocyte myeloid progenitors).

DETAILED DESCRIPTION OF THE EMBODIMENTS

Figure 1A:
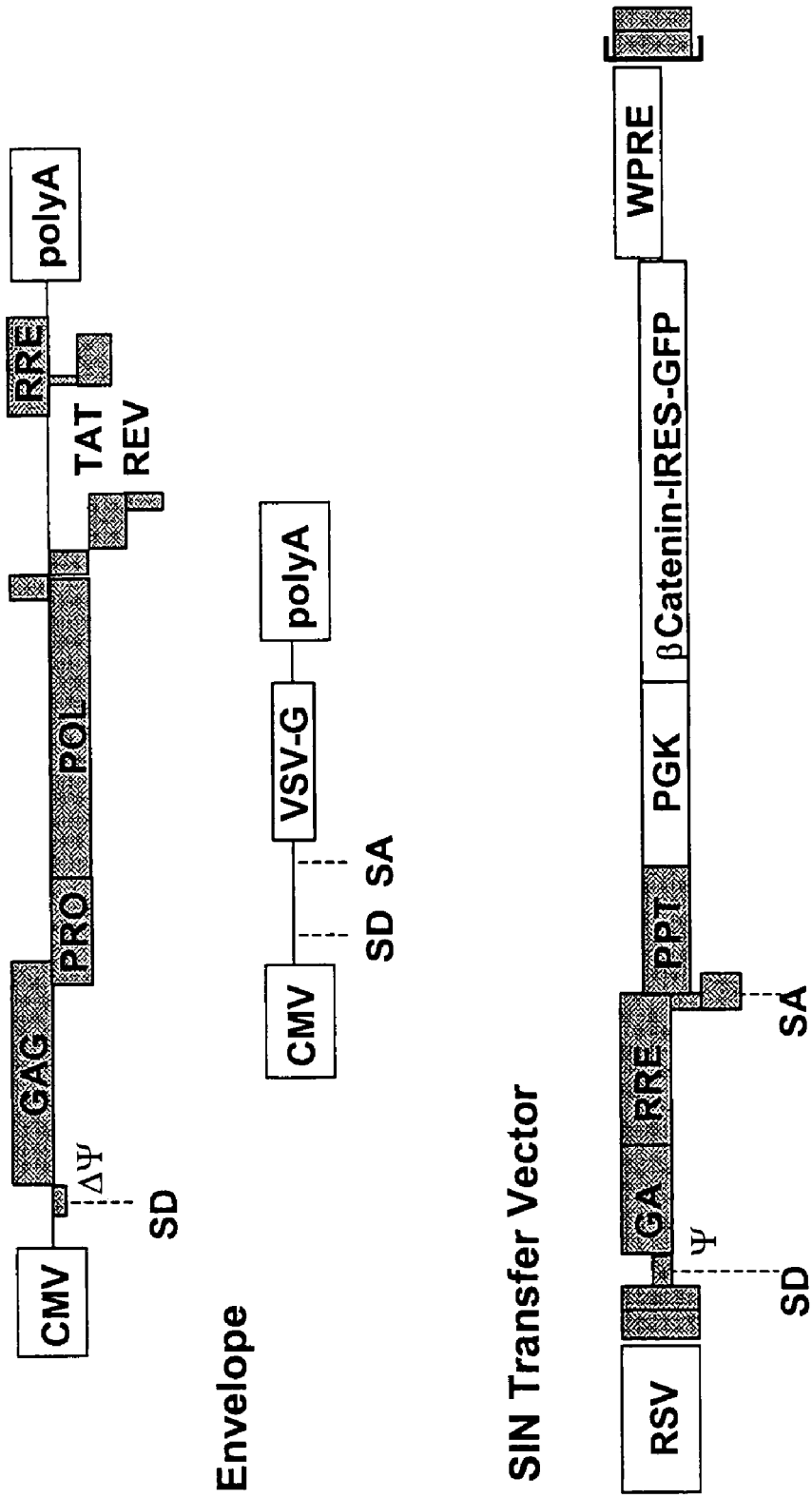
FIGS. 1A and 1B are schematics illustrating lentiviral vectors for the expression of β-catenin (1); and for the expression of detectable marker proteins operably linked to a β-catenin responsive transcriptional regulatory element (3).
Figure 1B:
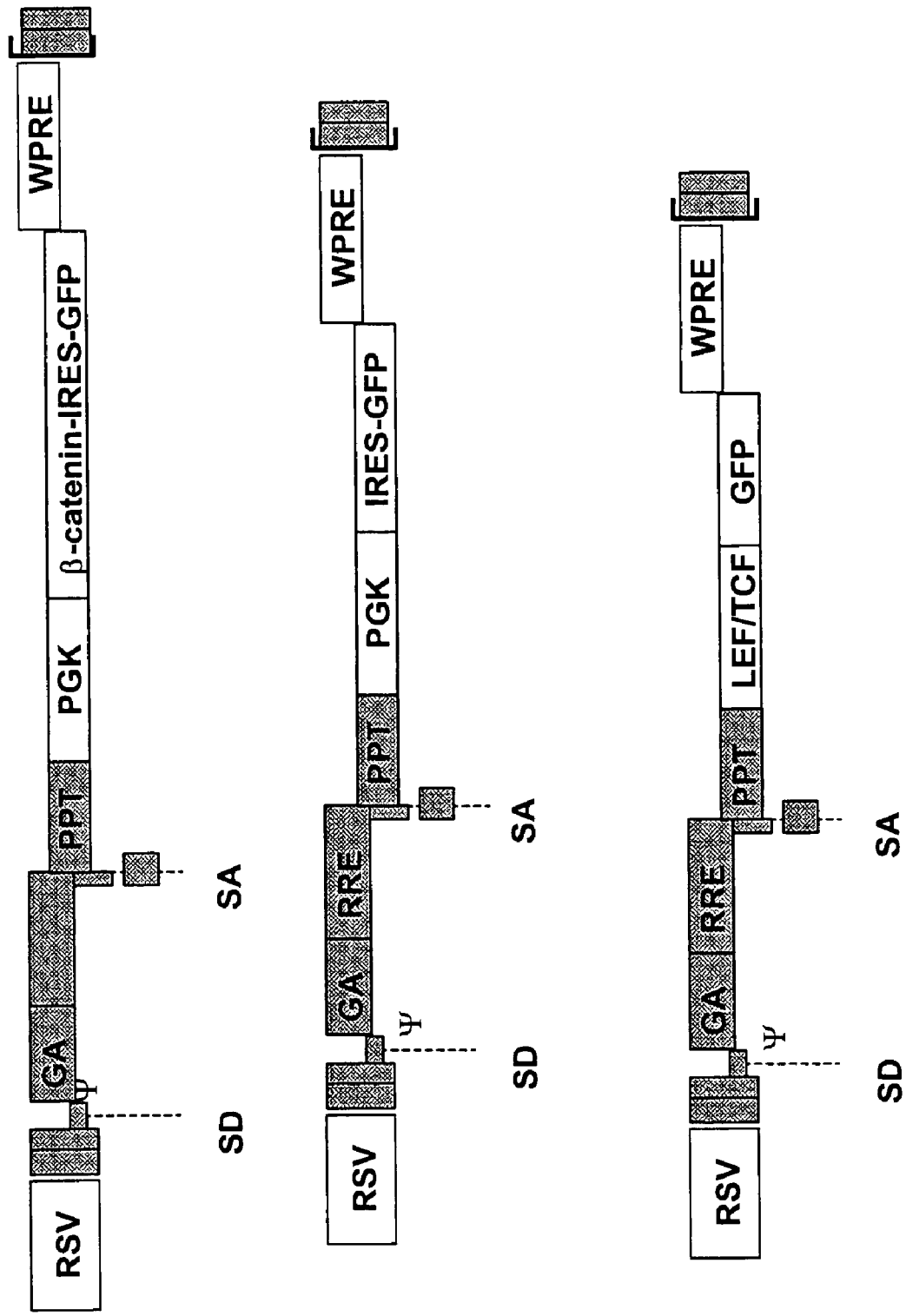

Methods and compositions are provided for the identification of stem cells and cancer stem cells, by introducing a nucleic acid construct encoding a detectable marker operably linked to a transcriptional response element regulated by β-catenin. Expression of the marker is indicative of activated β-catenin in the cell, and indicates that a cell is a stem cell. The method may be used to test whether a cell is a stem cell; and to isolate and identify stem cells in mixed populations of cells.

β-catenin is also identified as a target for the development of therapeutic moieties against hematopoietic tumors, i.e. leukemia and lymphoma cells, and against tumor stem cells. Methods include screening assays directed at β-catenin, or members of the β-catenin signaling pathway.

In another embodiment of the invention, the introduction of stabilized β-catenin into a hematopoietic cell that is altered in its ability to undergo apoptosis but which is not fully transformed is used to immortalize the cell. The immortalized cells are useful in screening assays, and in the analysis of pathways by which hematopoietic cells undergo transformation. Screening methods may involve conducting various types of assays to identify agents that modulate the expression or activity of β-catenin. Lead compounds and/or binding moieties identified during these screens can serve as the basis for the synthesis of more active analogs. Lead compounds and/or active analogs generated therefrom can be formulated into pharmaceutical compositions effective in treating hematopoietic tumors.

Association of β-Catenin with Hematologic Tumors

The data presented herein demonstrate that β-catenin is associated with hematologic tumors. Detection of inappropriate β-catenin activity, i.e. nuclear translocation, mutation, over-expression, etc., find use in diagnostic assays for detection and characterization of hematopoietic hyperproliferative diseases, as well as the use of β-catenin as a target for therapeutic agents. Hyperproliferative conditions of interest include myeloproliferative disorders, which are a group of disorders characterized by abnormal proliferation of one or more hematopoietic cell lines or connective tissue elements. The myeloproliferative disorders include polycythemia vera, myelofibrosis, chronic myelogenous (myelocytic) leukemia, and primary thrombocythemia. Some hematologists also include acute leukemia, especially erythroleukemia, and paroxysmal nocturnal hemoglobinuria. Each disorder is identified according to its predominant feature or site of proliferation. Myeloproliferative disorders sometimes terminate in acute leukemia.

Leukemias are malignant neoplasms of blood-forming tissues. Viral associated leukemias include Burkitt's lymphoma and human T-cell lymphotropic virus type I leukemias. Exposure to ionizing radiation and certain chemicals (e.g., benzene, some antineoplastic drugs) is associated with an increased risk of leukemia. Some genetic defects (e.g., Down syndrome, Fanconi's anemia) also predispose to leukemia.

Transformation to malignancy (through two or more steps) occurs in a single cell, with subsequent proliferation and clonal expansion. Usually, transformation occurs at the pluripotent stem or progenitor cell level, but sometimes it may involve a committed cell with capacity for more limited differentiation. The clone tends to be genetically unstable with features of heterogeneity and phenotypic evolution. In general, leukemic cells divide with longer cell cycles and smaller growth fractions than normal bone marrow cells, and they accumulate because of slowed apoptosis (programmed cell death).

Clinical and laboratory features of leukemia are caused by suppression of normal blood cell formation and organ infiltration. Inhibitory factors produced by leukemic cells or replacement of marrow space may suppress normal hematopoiesis, with ensuing anemia, thrombocytopenia, and granulocytopenia. Organ infiltration results in enlargement of the liver, spleen, and lymph nodes, with occasional kidney and gonadal involvement. Meningeal infiltration results in clinical features associated with increasing intracranial pressure (e.g., cranial nerve palsies).

Leukemias were originally termed acute or chronic based on life expectancy but now are classified according to cellular maturity. Acute leukemias consist of predominantly immature cells (usually blast forms); chronic leukemias, more mature cells. Acute leukemias are divided into lymphoblastic (ALL) and myelogenous (AML) types, which may be further subdivided by morphologic and cytochemical appearance or immunophenotype. Chronic leukemias are described as lymphocytic (CLL) or myelocytic (CML). Myelodysplastic syndromes represent progressive bone marrow failure but with an insufficient proportion of blast cells (<30%) for definite diagnosis of AML; 40 to 60% of cases evolve into AML.

Lymphomas include Hodgkin's lymphoma and non-Hodgkin's lymphomas, characterized as malignant monoclonal proliferation of lymphoid cells in sites of the immune system, including lymph nodes, bone marrow, spleen, liver, and GI tract. The course of NHL varies from indolent and initially well tolerated to rapidly fatal. A leukemia-like picture may develop in up to 50% of children and about 20% of adults with some types of NHL. NHL occurs more often than Hodgkin's disease. The incidence of NHL, particularly immunoblastic and small noncleaved (Burkitt's lymphoma) cell types, is increased in HIV patients. The Working Formulation classifies NHL into prognostic categories having therapeutic implications as follows: Low-grade lymphomas (38%): diffuse, small lymphocytic; follicular, small cleaved cell; follicular mixed, small and large cell. Intermediate-grade lymphomas (40%): follicular large cell; diffuse, small cleaved cell; diffuse mixed, small and large cell; diffuse large cell. High-grade lymphomas (20%): Immunoblastic lymphoma; lymphoblastic lymphoma; small noncleaved cell lymphoma (Burkitt's and non-Burkitt's type). Miscellaneous lymphomas (2%): composite lymphomas, mycosis fungoides, true histiocytic, other, and unclassifiable types.

CML is believed to arise as a consequence of clonal expansion of defective primitive hematopoietic progenitors. Using confocal fluorescence microscopy, intranuclear and cytoplasmic β-catenin expression is shown to be elevated in chronic myelogenous leukemic compared with normal bone marrow mononuclear cells and isotype controls. Five colour FACS analysis demonstrated a marked expansion of myeloid progenitors in CML samples compared with normal bone marrow or peripheral blood but equivalent numbers of hematopoietic stem cells. Notably, β-catenin expression was found to be elevated in CML compared with normal myeloid progenitors, while β-catenin expression was similar in CML and normal HSC.

Moreover, because β-catenin-induced activation of stem cell self-renewal has been shown to be mediated by binding of β-catenin to the transcription factor LEF/TCF, normal and CML patient HSC and myeloid progenitors were transduced with a lentiviral LEF/TCF-GFP vector to assay for intranuclear binding of β-catenin to its downstream target. Although normal and patient HSC displayed similar GFP levels after 7-10 days in culture, CML myeloid progenitors demonstrated greater GFP expression than their normal counterparts, indicative of increased nuclear translocation of β-catenin. Taken together, these experiments demonstrate that activation of the Wnt signaling pathway through over-expression of activated β-catenin in myeloid progenitors enhances their leukemic potential. β-catenin over-expression can be used diagnostically to detect cancer "stem cells" capable of propagating disease as well as therapeutically via targeted β-catenin inhibition using lentiviral transduction with known inhibitors of β-catenin such as axin and dickkopf.

In an animal model, c-kit+ pre-leukemic lpr/lpr bcl-2 cells were transduced with control vector or β-catenin vector, and after one day of culture were transplanted into sublethally irradiated RAG2-/-g-/- mice. The β-catenin vector significantly increased the tumorigenicity of the transplanted cells, resulting in leukemias. Whole bone marrow cells from such leukemic mice transplanted with β-catenin transduced cells, were then transplanted into sublethally irradiated RAG2-/-g-/- mice in order to propagate the leukemic phenotype, and were found to have a significantly greater potential for proliferation after serial transplantation.

Constructs for the Detection and Separation of Stem Cells

In one embodiment of the invention, a nucleic acid construct is introduced into a cell or population of cells, where the construct comprises sequences encoding a detectable marker, which marker is operably linked to a transcriptional response element regulated by β-catenin, herein termed a "detection construct". In the presence of nuclear β-catenin, the detectable marker is expressed, and indicates that a cell is a stem cell. In this aspect, the method may be used to determine whether a test cell is a stem cell. Viable cells expressing the marker can also be sorted, in order to isolate or enrich for the stem cells of interest. In this aspect, the methods may be used to enrich for known stem cells and to select for previously unknown stem cells.

A variety of vectors are known in the art for the delivery of sequences into a cell, including plasmid vectors, viral vectors, and the like. In a preferred embodiment, the vector is a retroviral or lentiviral vector. For example, see Baum et al. (1996) J Hematother 5(4):323-9; Schwarzenberger et al. (1996) Blood 87:472-478; Nolta et al. (1996) P.N.A.S. 93:2414-2419; and Maze et al. (1996) P.N.A.S. 93:206-210, Mochizuki et al. (1998) J Virol 72(11):8873-83. The use of adenovirus based vectors with hematopoietic cells has also been published, see Ogniben and Haas (1998) *Recent Results Cancer Res* 144:86-92.

The beta-catenin transcriptional response element (TRE) will comprise one or more nucleotide motifs that bind a transcription factor activated by β-catenin. In a preferred embodiment, the transcription factor is LEF/TCF (for a review, see Roose and Clevers (1999) Biochim Biophys Acta 1424(2-3):M23-37, herein incorporated by reference). Transcriptionally inert LEF/Tcf factors become potent transactivators upon interaction with beta-catenin in the nucleus. It may be noted that β-catenin is found in the cytoplasm, but its primary biological effects are seen when it is activated and translocated into the nucleus. Nucleotide elements responsive to this signaling pathway include, for example TBE1 (SEQ ID NO:1; CCTTTGATT) and TBE2 (SEQ ID NO:2; GCTTTGATC), which are contained on the human c-MYC promoter KpnI to PvuII fragment, see He et al. (1998) *Science* 281:1509; LEF/TCF binding motifs, (e.g. SEQ ID NO:3; CCTTTGATC; or SEQ ID NO:4; CCTTTGGCC) (Korinek et al. (1997) *Science* 275:1784-1787); LEF-1 binding sites, SEQ ID NO:5; GCTTTGATCTT (Shtutman et al. (1999) *Proc Natl Acad Sci USA* 96(10):5522-7), and otherwise as known in the art. There references are herein specifically incorporated by reference for their teaching of sequences responsive to LEF-1/TCF. The complement of these sequences may also be used, e.g. (SEQ ID NO:13) GATCAAAGGG.

In one embodiment of the invention, the β-catenin responsive TRE comprises one or more, two or more, three or more, etc. of a binding motif sequence (SEQ ID NO:12) $X^1$ C T T T G Pu T Py; where $X^1$ is G or C, Pu is purine and Py is pyrimidine. In a preferred embodiment the β-catenin responsive TRE comprises one or more, two or more, three or more, etc. of a binding motif sequence that is the complement of SEQ ID NO:12; (SEQ ID NO:14) 5' Pu A Py C A A A G $X^1$ 3', where $X^1$ is G or C, Pu is purine and Py is pyrimidine.

Operably linked to the β-catenin TRE is a detectable marker. Many such markers are known in the art, for example antibiotic resistance, color change of a substrate, expression of a recombinase, e.g. cre recombinase, FLP recombinase, pSR1 recombinase, etc., which is indirectly detected; expression of luminescence producing proteins, e.g. luciferase, green fluorescent proteins, etc.

In a preferred embodiment of the invention, the marker is a luminescence producing protein, preferably GFP. The native gene encoding this protein has been cloned from the bioluminescent jellyfish *Aequorea victoria* (Morin, J. et al., J Cell Physiol (1972) 77:313-318). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce. (Prasher, D. C. et al., Gene (1992) 111:229-233; Yang, F. et al., Nature Biotechnol (1996) 14:1252-1256; Cody, C. W. et al., Biochemistry (1993) 32:1212-1218.) Mutants of the GFP gene have been found useful to enhance expression and to modify excitation and fluorescence. GFP-S65T (wherein serine at 65 is replaced with threonine) may be used, which has a single excitation peak at 490 nm. (Heim, R. et al., Nature (1995) 373:663-664); U.S. Pat. No. 5,625,048. Other mutants have also been disclosed by Delagrade, S. et al., Biotechnology (1995) 13:151-154; Cormack, B. et al., Gene (1996) 173:33-38 and Cramer, A. et al. Nature Biotechnol (1996) 14:315-319. Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance. Various forms of GFP exhibit colors other than green and these, too, are included within the definition of "GFP" and are useful in the methods and materials of the invention. In addition, it is noted that green fluorescent proteins falling within the definition of "GFP" herein have been isolated from other organisms, such as the sea pansy, *Renilla reriformis*. Any suitable and convenient form of the GFP gene can be used in the methods of the invention.

Various techniques known in the art may be used to transfect the target cells, e.g. electroporation, calcium precipitated DNA, fusion, transfection, lipofection and the like. The particular manner in which the DNA is introduced is not critical to the practice of the invention.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the β-catenin gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

For detecting or selecting stem cells, the detection construct is introduced into a cell or population of cells, suspected of being or comprising stem cells. After introduction of the expression construct, the cells are maintained for a period of time sufficient to express the detectable marker, usually at least about 12 hours and not more than about 2 weeks, and may be from about 1 day to about 1 week.

The cells may be obtained from any mammalian species, e.g. equine, bovine, porcine, canine, feline, rodent, e.g. mice, rats, hamster, primate, etc., particularly human. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−180° C.) indefinitely. Populations of cells include putative stem cell clones, tumor samples, bone marrow samples, embryonic stem cells, organs, e.g. neural crest, gut, spleen, liver, umbilical cord blood, peripheral blood, mobilized peripheral blood, yolk sac, etc.

The expression of the detectable marker, where the marker is a fluorescent protein, can be monitored by flow cytometry, where lasers detect the quantitative levels of fluorophore. Flow cytometry, or FACS, can also be used to separate cell populations based on the intensity of fluorescence, as well as other parameters such as cell size and light scatter. Although the absolute level of staining may differ, the data can be normalized to a control.

In addition to expression of the β-catenin-regulated marker gene, the cells may be co-stained with antibodies specific for markers of interest, e.g. expression of c-kit, thy-1 (CD-90), lineage markers, CD34, growth factor receptors, and the like, as known in the art. Many progenitor and stem cells markers are known and used to distinguish these cell types.

The cells of interest may be separated from a complex mixture of cells by techniques that enrich for cells having the above characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for stem cell activity are achieved in this manner. The subject population may be at or about 50% or more of the cell composition, and preferably be at or about 75% or more of the cell composition, and may be 90% or more. The desired cells are identified by their surface phenotype, by the ability to self-renew, an essential property of stem cells. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for cells having activated β-catenin may be used in a variety of screening assays and cultures, as described below.

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogeneous thymic stromal cells (Small and Weissman [1996] *Scand J Immunol* 44:115-121).

In another aspect of the invention, a construct is used to deliver β-catenin, usually stabilized β-catenin, coding sequences, e.g. to immortalize targeted stem or progenitor cells by introduction of an exogenous nucleic acid expression vector into the cells. Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Such constructed may be referred to as "immortalizing constructs".

The term β-catenin, as used herein, is intended to refer to both wild-type and stabilized forms of the β-catenin protein, and to fusion proteins and derivatives thereof. Usually the protein will be of mammalian origin, although the protein from other species may find use. The protein is conserved between species, for example the human sequence is active in mouse cells. The sequences of many β-catenin proteins are publicly known. In one embodiment of the invention, a stabilized form of beta-catenin is used.

Beta-catenin becomes stabilized when proteasome-mediated proteolysis is inhibited and this leads to the accumulation of multi-ubiquitinated forms of beta-catenin (Aberle et al. (1997) EMBO J 16(13):3797-804). Substitution of the serine residues in the glycogen synthase kinase 3β (GSK3beta) phosphorylation consensus motif of beta-catenin inhibits ubiquitination and results in stabilization of the protein. Examples of stabilized β-catenins include those with the amino acid changes D32Y; D32G; S33F; S33Y; G34E; S37C; S37F; T41I; S45Y; and deletion of AA 1-173. A number of publications describe stabilized β-catenin mutations. For example, see Morin et al. (1997) Science 275(5307):1787-90; Palacios et al. (1998) Cancer Res 58(7):1344-7; Muller et al. (1998) Genes Chromosomes Cancer 22(1):37-41; Miyoshi et al. (1998) Cancer Res 58(12):2524-7; Zurawel et al. (1998) Cancer Res. 58, 896-899; Voeller et al. (1998) Cancer Res. 58, 2520-2526; etc.

The sequence of the beta-catenin polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. Deletions may further include larger changes, such as deletions of a domain or exon, providing for active peptide fragments of the protein. Other modifications of interest include tagging, e.g. with the FLAG system, HA, green fluorescent protein, etc. Such alterations may be used to alter properties of the protein, by affecting the stability, specificity, etc. The protein may be joined to a wide variety of other oligopeptides or proteins for a variety of purposes, particular for facilitating transport across membranes.

Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199: 537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

Genetic constructs may be removed from the target cells after expansion. This can be accomplished by the use of a transient vector system, or by including a heterologous recombination site that flanks the beta-catenin coding sequence. In this manner, after expansion the construct can be removed prior to use of the expanded cell population. Preferably a detectable marker, e.g. green fluorescent protein, luciferase, cell surface proteins suitable for antibody selection methods, etc. is included in the expression vector, such that after deletion of the construct the cells can be readily isolated that lack the exogenous beta-catenin. The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences with recombination mediated by Cre enzyme; frt sequences (Golic et al. (1989) *Cell* 59:499-509; O'Gorman et al. (1991) *Science* 251:1351-5; recombination mediated by the FLP recombinase), the recognition sequences for the pSR1 recombinase of *Zygosaccharomyces rouxii* (Matsuzaki et al. (1990) *J. Bacteriol.* 172: 610-8), and the like.

Expression vectors that provide for the transient expression in mammalian cells may be used. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient short term expansion of cells, but do not affect the long term genotype of the cell.

The immortalizing construct, which provides for modulation of the ability of a cell to proliferate, is introduced into the hematopoietic cells by any of a variety of different methods.

Preferably the hematopoietic cells are progenitor or stem cells, including myeloid progenitor cells, hematopoietic stem cells, lymphoid progenitor cells, multilineage progenitors, and the like. For a review of the lineages of hematopoietic stem cells and progenitors, see Wagers et al. (2002) Gene Ther. 9(10):606-12; Park et al. (2002) Blood 99(2):488-98; and Weissman et al. (2001) Annu Rev Cell Dev Biol 17:387-403, herein each incorporated by reference.

Preferably the cells into which the β-catenin expressing sequence is introduced will be altered so as to have one or more "hits", or genetic alterations that lead to decreased ability to correctly regulate cell proliferation. An example of such cells may be found in U.S. Pat. No. 5,614,397, Lagasse et al., herein incorporated by reference. Progenitor cells of interest include the cells of myeloid and lymphoid series, particularly the cells of the myeloid series and most particularly, the cells of the myelomonocytic series, especially neutrophils.

The methods used for introduction of the β-catenin include "ex vivo" transfection of a target cell, which target cell may be the target cell, e.g. a progenitor cell; or a stem cell that gives rise to the target cell. Methods of interest include the use of naked DNA, DNA-liposome conjugates, retroviral vectors, lentiviral vectors, etc. followed by culture of the cells in vitro, or implantation of the transformed cells into the host mammal, such as a mouse or a human.

For introducing a transgene that is to be nonhomologously integrated and form a transgenic nonhuman animal (e.g., mouse), pronuclear microinjection of fertilized eggs (e.g., mouse) is preferred. For making transgenic nonhuman animals which include homologously targeted nonhuman animals, embryonal stem cells (ES cells) are generally preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford:IRL Press), p. 71-112) may be used for homologous gene targeting. Other suitable ES lines include, the E14 line (Hooper et al. (1987) Nature 326:292-295), the D3 line (Doetschman et al. (1985) J. Embryol Exp. Morph. 87:27-45), and the CCE line (Robertson et al. (1986) Nature 323:445-448). The success of generating a mouse line from ES cells depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females. Resultant transgenic mice having a gene of interest that modulates the lifespan of cells operably linked to a hematolymphoid cell expressing gene regulatory sequence of interest such as MRP8 or MRP14 are screened for the presence of the correctly targeted construct and/or transgene(s) by PCR or Southern blot analysis on tail or other tissue biopsy DNA so as to identify transgenic mice having the gene of interest in the desired location(s). Such transgenic animals are useful sources of transgenic hematopoietic stem cells that express the gene of interest in specific progeny cells such as neutrophils. The transgenic hematopoietic stem cells are useful for transplantation and immunomodulatory drug screening assays.

The stem cells isolated by the methods of the invention, and cells and animals generated by introduction of an immortalizing construct find use in compound screening, for the identification of genes expressed in stem cells, for therapies utilizing stem cells, and the like.

Compound screening may be performed using an in vitro model, a genetically altered cell or animal, or purified protein corresponding to β-catenin. Transgenic animals or cells derived therefrom are also used in compound screening.

Compound screening identifies agents that modulate function of the β-catenin. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. Knowledge of the 3-dimensional structure of the encoded protein, derived from crystallization of purified recombinant protein, could lead to the rational design of small drugs that specifically inhibit activity. These drugs may be directed at specific domains.

The term "agent" as used herein describes any molecule, e.g. protein or pharmaceutical, with the capability of altering or mimicking the physiological function of β-catenin and self-renewal of hematopoietic cells. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Compounds that are initially identified by any of the foregoing screening methods can be further tested to validate the apparent activity. The basic format of such methods involves administering a lead compound identified during an initial screen to an animal that serves as a model for humans and then determining activity. The animal models utilized in validation studies generally are mammals. Specific examples of suitable animals include, but are not limited to, primates, mice, and rats.

Active test agents identified by the screening methods described herein that inhibit tumor growth can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Some of the diagnostic and prognostic methods that involve the detection of cells comprising activated p-catenin begin with the lysis of cells and subsequent purification of nucleic acids from other cellular material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample.

A number of methods are available for analyzing nucleic acids for the presence of a specific sequence, e.g. upregulated or downregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. ALEXA dyes (available from Molecular Probes, Inc.); fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes is then contacted with the cells and the probes allowed to hybridize. Excess probe is digested, washed away and the amount of hybridized probe measured. This approach is described in greater detail by Nucleic Acid Hybridization: A Practical Approach (Hames, et al., eds., 1987).

A variety of so-called "real time amplification" methods or "real time quantitative PCR" methods can also be utilized to determine the quantity of mRNA present in a sample. Such methods involve measuring the amount of amplification product formed during an amplification process. Fluorogenic nuclease assays are one specific example of a real time quantitation method that can be used to detect and quantitate transcripts. In general such assays continuously measure PCR product accumulation using a dual-labeled fluorogenic oligonucleotide probe—an approach frequently referred to in the literature simply as the "TaqMan" method. Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, each of which is incorporated by reference in its entirety.

Screening for expression of β-catenin may be based on the functional or antigenic characteristics of the protein, including the nuclear localization of the protein. Various immunoassays designed to detect polymorphisms may be used in screening. Detection may utilize staining of cells or histological sections, performed in accordance with conventional methods, using antibodies or other specific binding members that specifically bind to β-catenin. The antibodies or other specific binding members of interest are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

Other features and advantages of the invention will be apparent from the description of the preferred embodiments, and from the claims. The following examples are offered by way of illustration and not by way of limitation.

EXPERIMENTAL

Example 1

Figure 2:
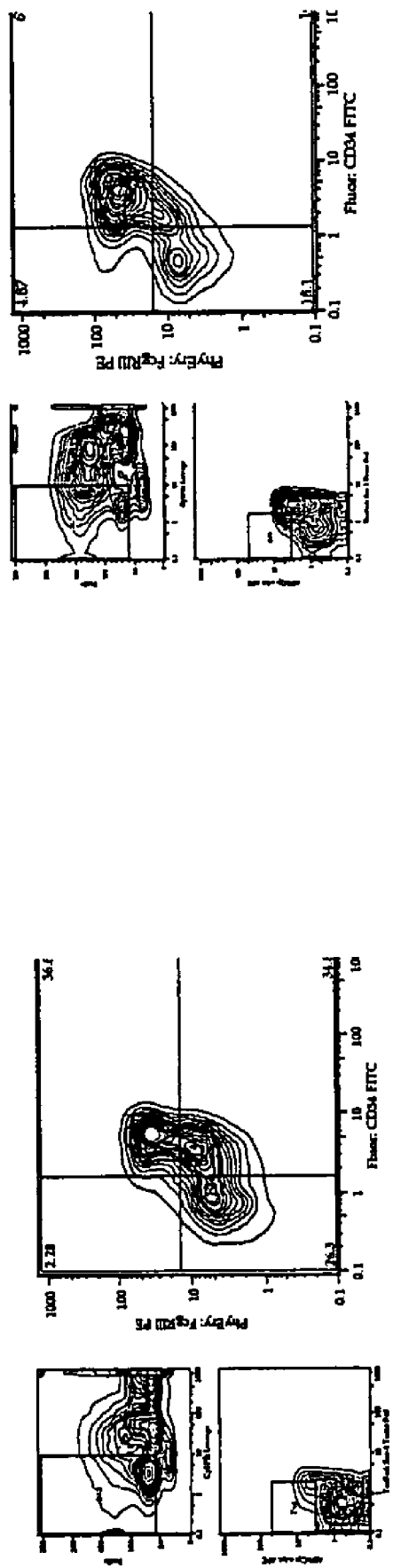
FIG. 2 is a FACs plot comparing cells from a control animal and from an animal transplanted with β-catenin transformed cells.

Sorting and Transplantation of Myeloid Progenitors and Hematopoietic Stem Cell (HSC) Enriched Populations from Leukemic Mice Leukemic mouse bone marrow progenitor populations were analyzed and sorted using 5 color flow cytometric analysis (FACS Vantage) and compared with those of control animals. Briefly, bone marrow was flushed from the femurs, a single cell suspension was made by passage through a 25 gauge needle and after washing the cells were incubated with a biotinylated lineage antibody cocktail consisting of CD3, 4, 8, B220, IL-7 Receptor, Thy 1.1, Mac-1, Gr-1 and Ter 119 for 30 minutes followed by washing and addition of Dynabeads for 30 minutes. Lin+ cells were then removed using a Dynal magnetic particle concentrator. Progenitors were stained with anti-CD34 FITC, c-Kit APC, Sca-1 Texas Red and FcγRIII PE for 30 minutes followed by staining with Avidin Cy5 PE for 30 minutes and finally the addition of propidium iodide. Equivalent numbers (5000/mouse) of GMP (c-kit$^+$ sca$^-$ lineage$^-$ FcγRIII$^+$ CD34$^+$) and HSC (c-kit$^+$, Sca1$^+$, lineage$^-$) cells were transplanted retro-orbitally into anaesthetized immunocompromised (RAG2$^{-/-}$ FcγR$^{-/-}$ or nu/nu) sublethally irradiated (380 rads) mice. An expansion of HSC and GMP were noted in 1°, 2° and 3° leukemic animals, as shown in FIG. 2.

Figure 3:
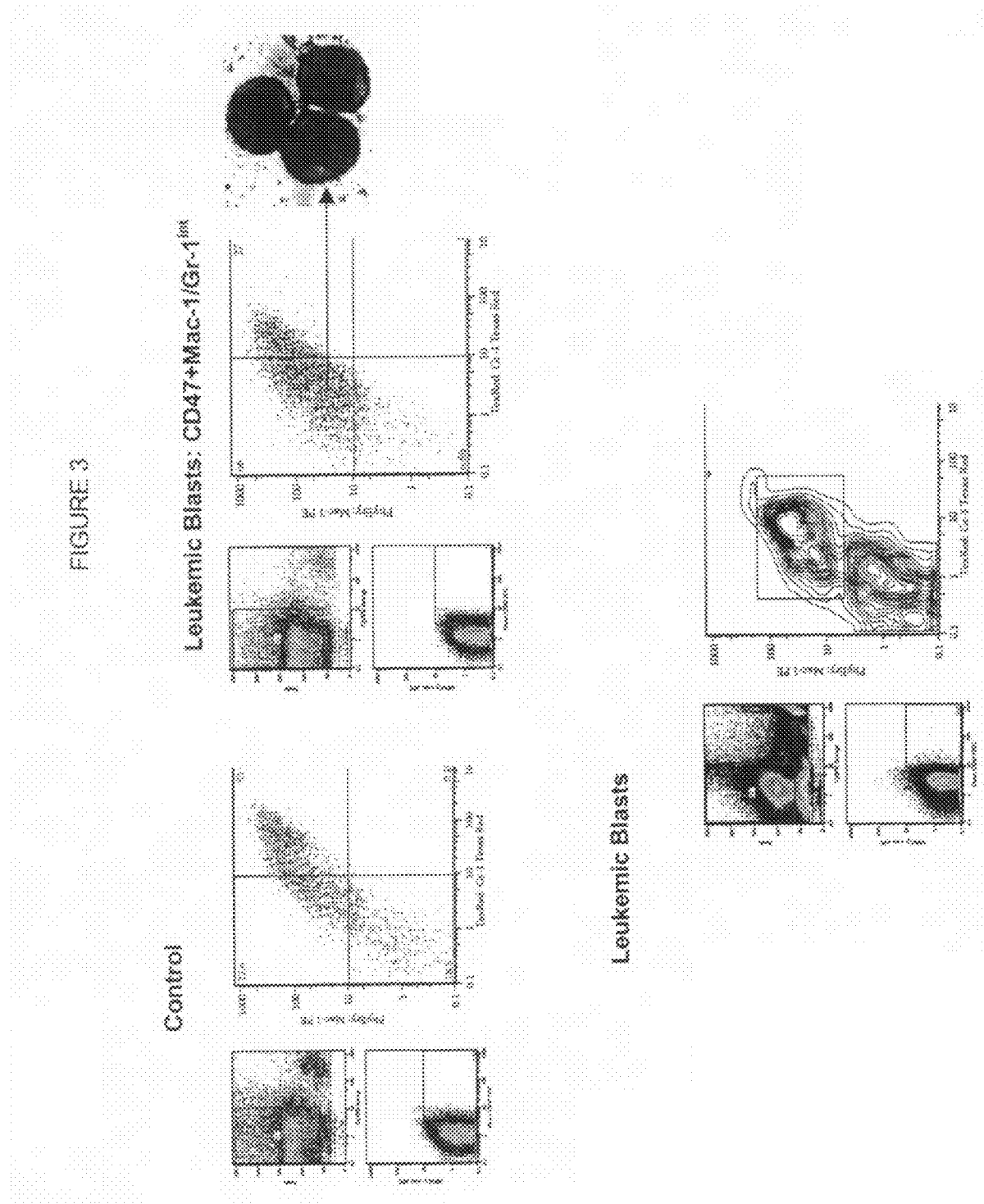
FIG. 3 is a characterization of leukemic blasts comprising β-catenin.

Leukemic mouse bone marrow and spleen blasts were analyzed and sorted using the FACS Vantage after staining for lineage$^+$ cells as described above, except that Mac-1 and Gr-1 were not included in the lineage cocktail. Cells were stained with CD47 FITC, Mac-1 PE, Gr-1 Texas Red and c-kit APC. Blasts were enriched within the CD47$^+$, Mac-1/Gr-1 intermediate, c-Kit low population and were abundant in marrow and spleen of serially transplanted leukemic animals, as shown in FIG. 3.

Engraftment of transplanted cells was assessed via FACS Scanford analysis of intracellular human Bcl-2 FITC staining of Mac-1/Gr-1 PE costained, fixed (paraformaldehyde) and permeabilized (0.3% saponin) marrow or spleen compared with normal controls, as shown in FIG. 4.

Transduction of Bone Marrow Cells. Bone marrow was flushed from the femurs and tibias of nonleukemic Fas$^{lpr/lpr}$-MRP8-Bcl2 mice aged 6-10 weeks. Red blood cells were lysed with ammonium chloride, and the remaining cells were labeled with a biotinylated anti-c-kit antibody and avidin-conjugated magnetic beads. The c-kit-positive fraction was then enriched using the Miltenyi MACS magnetic purification system. The c-Kit+ fraction was then placed in tissue culture, in X-Vivo15 media with beta-mercaptoethanol, glutamate and 50 ng/ml Stem Cell Factor. Half of the cells received PGK-β-catenin-IRES-GFP lentiviral vector, and half of the cells received PGK-IRES-GFP lentiviral vector. The cells were incubated overnight, and the next day were injected intravenously into Rag–/– FcγR –/– recipients that were sublethally irradiated (380 rads). 8 mice were injected with beta-catenin transduced cells and 8 mice were injected with control vector-transduced cells. 6 of the 8 mice receiving beta-catenin-transduced cells became leukemic, within 7 to 10 weeks of transplant. None of the mice receiving control vector-transduced cells became sick (still alive 20 weeks later). Cells from the leukemic mice have been serially transferred and caused leukemia in a significant proportion of recipients, when transplanted into tertiary transplants so far (Table 1).

TABLE 1

| | # of mice transplanted | Cells transplanted | # of leukemic mice |
|---|---|---|---|
| 1° | 8 | c-Kit+ with activated β-catenin | 7 |
| 2° | 12 | Whole bone marrow | 6 |
| 3° | 4 | HSC | 0 |
| 4° | 9 | GMP | 8 |

Lentiviral Vectors. The gene transfer vectors that carry the desired sequences are packaged into viral particles and secreted into 293T cell supernatant upon cotransfection with plasmids expressing the appropriate packaging molecules. Two of the vectors used in these experiments contained the human phosphoglycerate kinase (PGK) promoter driving expression of β-catenin-IRES-GFP or just IRES-GFP as a control. The third vector contained a LEF/TCF-responsive promoter driving expression of GFP. The LEF/TCF responsive element has the sequence,

```
                                          (SEQ ID NO: 13)
CAGCTGAAGCTTGCATGCCTGCAGGATCAAAGGGGGTAAGATCAAAGGGG
                      1                 2

GTAAGATCAAAGGTCTAGAGGGTATATAATGGATCCGGTA.
     3
```

The binding sites (1, 2, and 3) are underlined, as is the TATA box.

Example 2

Analysis of β-Catenin Expression by Normal Versus Leukemic Cells

Ficoll-enriched mononuclear populations from normal or CML peripheral blood or bone marrow and the CML blast crisis cell line, K562, were stained with anti-β-catenin Alexa-594 (red) conjugated antibody and counterstained with Hoechst (blue) for nuclear visualization and then analyzed for cytoplasmic versus nuclear localization of β-catenin using a dual photo Zeiss LSM confocal fluorescence microscope. Both cytoplasmic and nuclear β-catenin expression were higher in K562 and CML mononuclear cells compared with normal cells.

Figure 5:
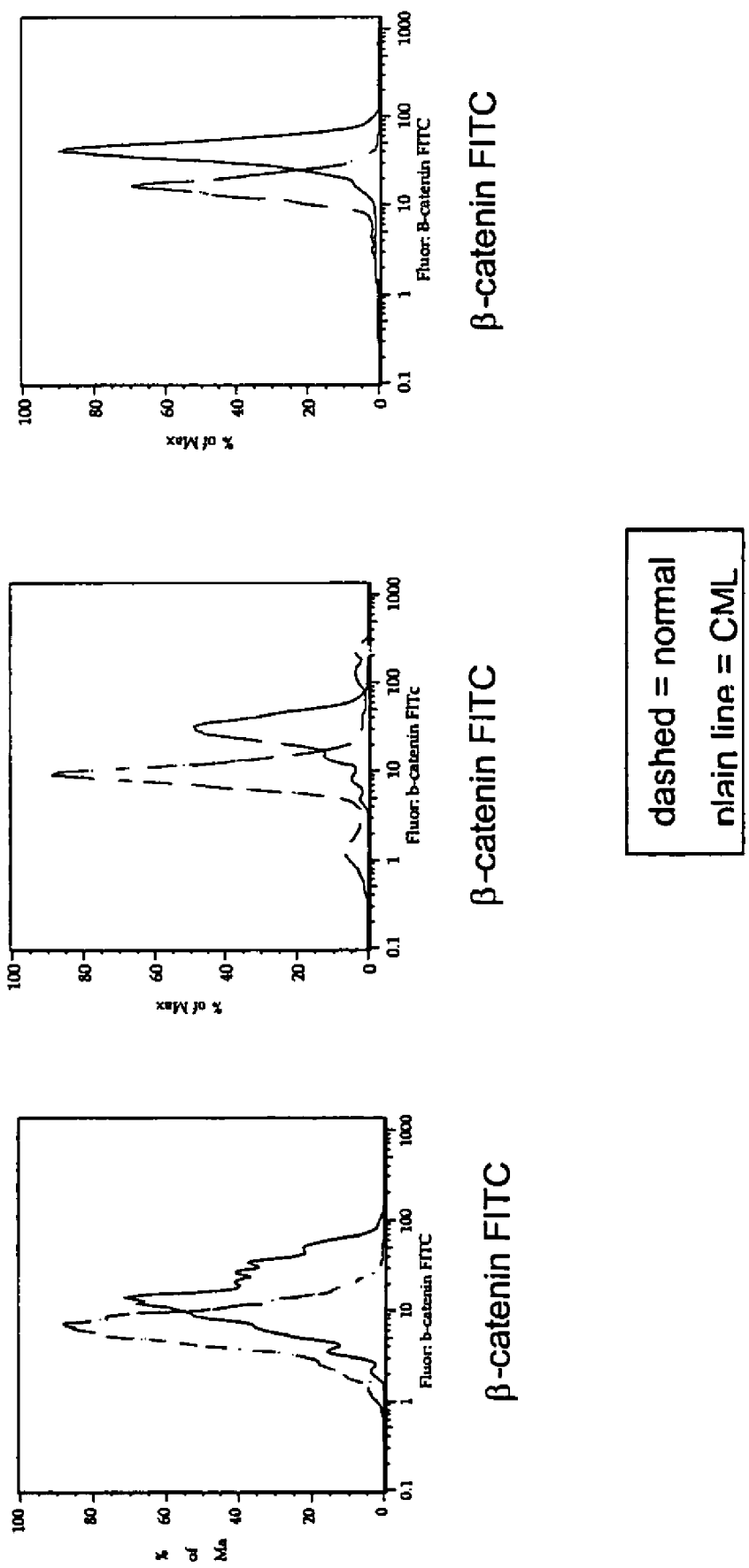
FIG. 5 depicts the increase in expression of β-catenin by CML myeloid progenitors.
Figure 6:
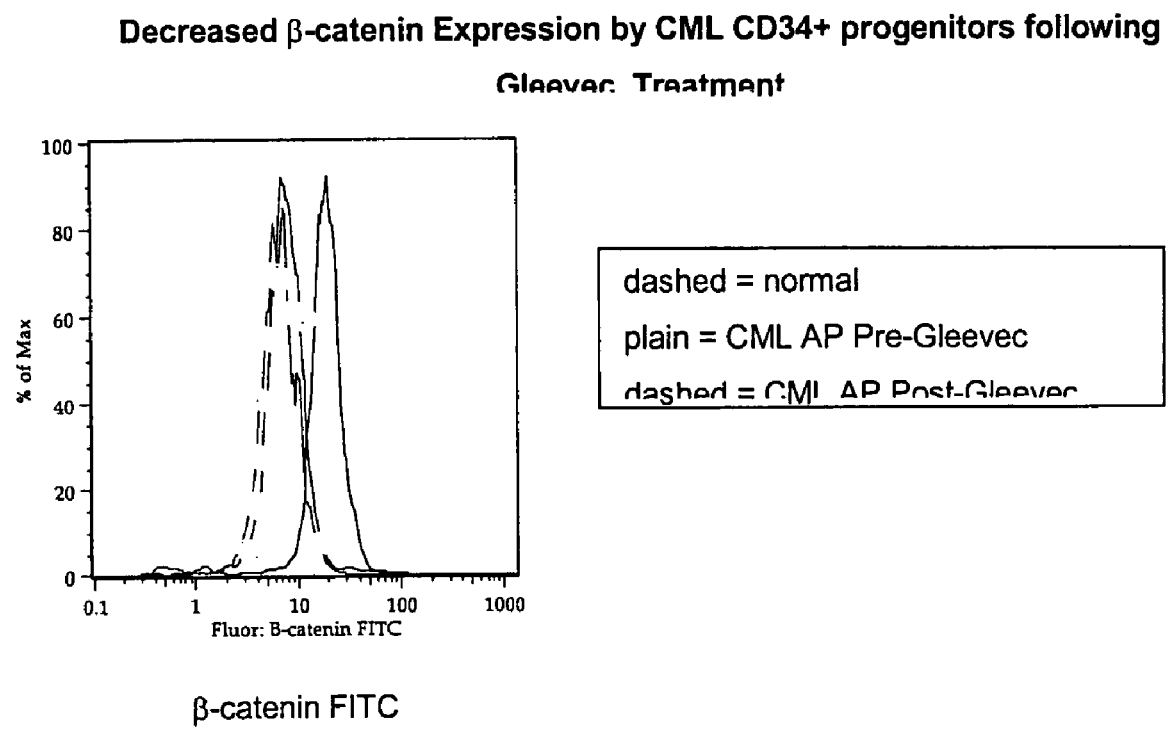
FIG. 6 depicts decreased β-catenin expression by CML CD34$^+$ progenitors following Gleevec treatment.

Human hematopoietic stem and myeloid progenitor cell populations were stained, analyzed and sorted with the aid of a FACS Vantage using a modification of previously described methodology (Manz et al P.N.A.S. (2002) 99:11872-11877). Briefly, mononuclear and CD34+ normal or CML chronic phase (CP), accelerated phase (AP) or blast crisis (BC) peripheral blood and bone marrow cells were stained for expression of lineage markers including CD2, 3, 4, 7, 8, 10, 11b, 14, 19, 20, 56 and Glycophorin A with the aid of Cy-5 PE labeled antibodies followed by staining with CD34 APC, CD38 Biotin, IL-3Rα PE for myeloid progenitors and CD90 PE for HSC and finally by Streptavidin Texas Red to detect CD38 biotin labeled cells, shown in FIG. 5 and FIG. 6. Cells were fixed with paraformaldehyde (4%) and then permeabilized (0.3% saponin) and stained with anti-β-catenin FITC overnight.

LEF/TCF-GFP Expression Following Lentiviral Transduction of Normal versus Leukemic Cells. HSC and progenitor cell populations were stained, analyzed and sorted using a FACS vantage as described previously (Manz et al PNAS 2002 vol 99; 11872-11877). Hematopoietic stem and progenitor populations were clone sorted (200-1000 cells/well) directly into 96 well plates containing 150 μl of Iscoves Modified Dulbecco's media (IMDM) supplemented with 10% fetal bovine serum, glutamine, antibiotics (Pen-Step) and cytokines including IL-6 (10 ng/ml), Flt3 ligand (50 ng/ml), stem cell factor (SCF; 50 ng/ml) and thrombopoietin (TPO; 10 ng/ml). LEF/TCF-IRES-GFP vector (1/100) or no vector was added to wells, cells were incubated in a 37° C., 7% $CO_2$ incubator for 7 to 10 days and then analyzed qualitatively for GFP expression with the aid of an inverted fluorescence microscope and quantitatively for GFP expression using FACS analysis (FACS Vantage). The data are shown in FIG. 7.

Example 3

HSCs in vivo normally signal via LEF/TCF elements. It was determined whether HSCs in vivo utilize signals associated with the Wnt/Fzd/beta-catenin pathway. Sorted KTLS HSCs were infected with vectors carrying the LEF-1-TCF reporter driving expression of destabilized GFP (TOP-dGFP) or control reporter construct carrying mutations in the LEF/TCF binding sites (FOP-dGFP), and transplanted into lethally irradiated mice. The HSCs were then transplanted into groups of irradiated recipient mice and recipient bone marrow examined after 14 weeks to determine whether donor HSCs demonstrated reporter activity. In the representative example shown, donor derived HSCs infected with TOP-dGFP were found to express GFP in 29% of the cells while HSCs from the recipient mouse were negative for GFP. Moreover, only 2.5% of HSCs transduced with the control FOP-dGFP reporter expressed GFP, demonstrating that functional LEF-TCF binding sites were specifically required for KTLS HSC expression of GFP.

Purified wild type HSCs were sorted by FACS and infected with one of two lentiviral reporter constructs: one containing LEF-TCF binding sites linked to a destabilized GFP (TOP-dGFP), and the other containing mutated LEF-TCF binding sites linked to destabilized GFP (FOP-dGFP). 6 hours after infection HSCs were transplanted into three lethally irradiated recipient mice, which were analyzed after 14 weeks. Donor derived HSC containing populations were distinguished from host derived HSC containing population by use of the allotypic marker CD45(Ly5). As a control, donor-derived HSCs carrying mutated LEF-TCF reporter as well as the recipient mouse HSCs were found to be GFP negative. Purified HSCs infected with the LEF-TCF reporter linked to either a destabilized GFP (TOP-dGFP) or a non-destabilized GFP (TOP-GFP) were stimulated in vitro with control media or with 100 ng/ml Wnt3A, and the extent of GFP expression monitored by FACS analysis.

Beta-catenin upregulates HoxB4 and Notch1 in HSCs. It was tested whether HSCs expressing activated beta-catenin upregulated HoxB4 and Notch 1, both genes that have previously been implicated in HSC proliferation and self-renewal by in vitro and in vivo assays. By using real time PCR analysis on HSCs infected with either beta-catenin or control vector, we found that HoxB4 was upregulated an average of 3.5 fold and Notch1 was upregulated 2.5 fold. In contrast, GAPDH expression was not differentially regulated as a consequence of beta-catenin expression and was used as a control. These data show for the first time that genes so far identified as regulators of HSC self-renewal may be related and perhaps act in a molecular hierarchy.

Methods

Mice. C57Bl/Ka Ly5.1, Thy1.1, C57Bl/Ka Ly5.2, Thy1.1 mice and AKR/J mice were housed in SPF facilities and used at 6-10 weeks of age. Mice were bred and maintained on acidified water in the animal care facility.

HSC isolation. HSC were sorted from mouse bone marrow using antibodies as described by Domen et al. (2000) *J Exp Med* 191:253-64. All cell sorting and FACS analysis was carried out on a FACSVantage (Becton Dickinson) at the Stanford shared FACS facility and the Duke Cancer Center FACS facility. Cells were sorted and reanalyzed based on expression of c-kit, Sca-1, low levels of Thy1.1, and low to negative levels of lineage markers (Lin).

Cell Cycle Analysis. Retrovirally transduced HSC were harvested from cultures and stained with Hoechst 3342 (Molecular Probes) at 37° for 45 minutes in Hoechst Medium. Cells were then washed, and analyzed by Flow cytometry to determine the cell cycle profile of $GFP^+$ cells.

Retroviral production and infection. Virus was produced by triple transfection of 293T cells with MSCV constructs along with gag-pol and VSVG constructs. Viral supernatant was collected for three days and concentrated 100 fold by ultracentrifugation at 50,000 g. For viral infection, 10,000 HSC were sorted into wells of a 96 well plate, and cultured o/n in the presence of SLF (30 ng/ml) (R&D systems). After 12 hours, concentrated retroviral supernatant was added to the cells at a 1:1 ratio. Cells were then incubated at 32° for 12 hours and 37° for 36 hours before $GFP^+$ cells were sorted for in vitro and in vivo assays. Lentiviruses used were produced as described below under lentiviral reporter assays.

In vitro HSC proliferation Assays. Freshly purified or virally transduced HSCs were plated at one to twenty cells per well in Terasaki plates using the single cell deposition unit and clonecyte software (Becton Dickinson Immunocytometry systems). Cells were sorted into wells containing serum free media (X-vivo 15, BioWhittaker) supplemented with $5\times10^{-5}$M 2-Mercaptoethanol and the indicated growth factors. Proliferation was monitored by counting the number of cells in each well at defined intervals. For longer-term cultures, transduced HSCs were plated into 96 well plates in the absence or presence of SLF (1 ng/ml), and the number of cells generated monitored by cell counting at defined intervals. For longer-term cultures, 10,000 transduced HSCs were plated into 96 well plates in the absence or presence of SLF (1 ng/ml), and the number of cells generated monitored by cell counting at defined intervals.

In vivo analysis of HSC function. Virally transduced HSC were cultured in vitro and injected retro-orbitally into groups of 4-6 recipient mice irradiated with 9.5 Gy using a 200 kV x-ray machine, along with 300,000 rescuing host total bone marrow or Sca-1 depleted cells. Host mice were given antibiotic water (1.1 g/L neomycin sulfate and 106 U/L polymyxin B sulfate) after irradiation. Transplanted mice were bled at regular periods to determine the percent of the hematopoietic compartment contributed by the donor cells. Donor and host cells were distinguished by allelic expression of CD45 (Ly5) or expression of the BCl2 transgene.

Lentiviral Reporter Assays

Vector Production. The EGFP or the d2-EGFP gene (destabilized, half-life of 2 hours; Clontech) was cloned downstream of a LEF/TCF-responsive promoter, containing 3 LEF/TCF binding motifs and a TATA box (Korinek et al. (1997) Science 275:1784-1787). This cassette was then cloned into a self-inactivating lentiviral vector plasmid (Follenzi et al. (2000) Nat Genet 25:217-22). Vector stocks were prepared and concentrated as previously described. Briefly, 293T cells were transfected with the transfer vector plasmid, the VSV-G envelope-encoding plasmid pMD.G, and the packaging plasmid CMVΔR8.74. The supernatant was harvested, ultracentrifuged and the vector pellet resuspended in a small volume of PBS/0.1% BSA. Similar constructs have been shown to transfect and their encoded genes be expressed in non-dividing HSCs (Uchida et al. (1998) Proc Natl Acad Sci 95:11939-44).

In vivo readout of LEF-TCF reporters. Double-sorted KTLS HSC were purified from HZ/Ly5.2/Thy1.1 mice by previously published methods. Cells were incubated in X-Vivo15 with glutamate, mercaptoethanol, pen/strep and a cocktail of cytokines consisting of 10 ng/ml IL-11, 10 ng/ml TPO, 50 ng/ml SCF, 50 ng/ml Flt-3L. The cells were incubated at 37° C., 7% $CO_2$ for 6 hours to overnight and transplanted into lethally irradiated congenic recipients (BA or B6/Ka). Each lethally irradiated mouse received 500 transduced HSC, along with $3 \times 10^5$ bone marrow mononuclear cells of the recipient strain. Mice were analyzed more than 14 weeks later (range 14 to 24 wks). For analysis, bone marrow was flushed and enriched for c-kit+ cells using AutoMACS. The Kit+ fraction was then stained with a Cy5-PE conjugated lineage cocktail (CD3, CD4, B220, Gr-1, Mac-1, Ter119), PE-conjugated Ly5.2, APC-conjugated c-kit, and TR-conjugated Sca-1 and analyzed by flow cytometry.

In vitro readout of LEF-TCF reporters. KTLS HSC were purified from BA mice and double-sorted directly into media (IMDM/10% FBS plus IL-11, TPO, SCF and Flt-3L as above). Cells were aliquotted into 96-well plates, 500 to 1000 cells per well. OT-GFP vector was added to the appropriate wells at a dilution of 1:100. Wnt3a was added to the appropriate wells at a dilution of 1:1000 in the presence of random methylated beta cyclodextrin from CTD, Inc. Wells not receiving Wnt3a got 1:1000 CHAPS instead. Cells were harvested 5 days later, stained with PI to exclude nonviable cells, and analyzed for GFP expression.

Real Time PCR analysis. 75,000 wildtype HSCs were cultured with either beta-catenin-IRES-GFP or control IRES-GFP lentiviruses. After two days in culture, infected cells were isolated on the basis of GFP expression. RNA was prepared using Trizol® (Invitrogen) and linearly amplified using a modified Eberwine synthesis. 500 ng of each amplified RNA was converted to first strand cDNA using SuperScript™ II reverse transcriptase (Invitrogen) and analyzed for differential gene expression by real time PCR. cDNAs were mixed with FastStart Master SYBR Green polymerase mix (Roche) and primers for GAPDH (forward, SEQ ID NO: 6; 5'-CCTGGAGAAACCTGCCAAGTATG and reverse, SEQ ID NO:7, 5'-AGAGTGGGAGTTGCTGTTGAAGTC), HoxB4 (forward, SEQ ID NO:8, 5'-GCACGGTAAAC-CCCAATTA and reverse, SEQ ID NO:9; 5'-GGCAACT-TGTGGTCTTTTTT), and Notch1 (forward, SEQ ID NO:10; 5-GCAGCCACAGAACTTACCACTCCAG and reverse, SEQ ID NO:11; 5'-TAAATGCCTCTGGAATGTGGGT-GAT). Real time PCR was performed using a LightCycler® (Roche) and real time data analyzed using LightCycler® software.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the presence of chronic myelogenous leukemia (CML) stem cells, the method comprising:
measuring expression of activated β-catenin in a human blood or bone marrow sample from an individual suspected of having CML stem cells, wherein increased expression of activated β-catenin in $CD34^+$ $CD38^+$ myeloid progenitor cells present in said blood or bone marrow sample, relative to expression of activated β-catenin in a normal sample, is indicative of the presence of CML stem cells.

2. The method of claim 1, wherein the activated β-catenin is detected with antibodies that specifically bind to β-catenin.

3. The method of claim 2 wherein the antibodies are added to a cell sample, and incubated for a period of time sufficient to allow binding to a β-catenin epitope.

4. A method for determining the presence of leukemia cells in a sample, the method comprising:
measuring β-catenin in a human hematopoietic cell sample wherein increased expression of β-catenin in myeloid progenitor cells, relative to that of a normal sample, is indicative of the presence of leukemia stem cells.

5. The method of claim 4, wherein the myeloid progenitor cells are $CD34^+CD38^+$.

6. The method of claim 4, wherein the leukemia cells are chronic myelogenous leukemia cells.

7. The method of claim 4, wherein the β-catenin is detected with antibodies that specifically bind to β-catenin.

8. The method of claim 1, comprising determining the presence of increased intranuclear β-catenin.

9. The method of claim 4, comprising determining the presence of increased intranuclear β-catenin.

\* \* \* \* \*

SEQUENCE LISTING

```
<160> NUMBER OF SEQ ID NOS: 15

<210> SEQ ID NO 1
<211> LENGTH: 9
<212> TYPE: DNA
<213> ORGANISM: Homo sapiens

<400> SEQUENCE: 1 cctttgatt                                                          9

<210> SEQ ID NO 2
<211> LENGTH: 9
<212> TYPE: DNA
<213> ORGANISM: Homo sapiens

<400> SEQUENCE: 2 gctttgatc                                                          9

<210> SEQ ID NO 3
<211> LENGTH: 9
```

```
<212> TYPE: DNA
<213> ORGANISM: Homo sapiens

<400> SEQUENCE: 3 cctttgatc                                                          9

<210> SEQ ID NO 4
<211> LENGTH: 9
<212> TYPE: DNA
<213> ORGANISM: Homo sapiens

<400> SEQUENCE: 4 cctttggcc                                                          9

<210> SEQ ID NO 5
<211> LENGTH: 11
<212> TYPE: DNA
<213> ORGANISM: Homo sapiens

<400> SEQUENCE: 5
gctttgatct t                                                      11

<210> SEQ ID NO 6
<211> LENGTH: 23
<212> TYPE: DNA
<213> ORGANISM: Homo sapiens

<400> SEQUENCE: 6
cctggagaaa cctgccaagt atg                                         23

<210> SEQ ID NO 7
<211> LENGTH: 24
<212> TYPE: DNA
<213> ORGANISM: Homo sapiens

<400> SEQUENCE: 7
agagtgggag ttgctgttga agtc                                        24

<210> SEQ ID NO 8
<211> LENGTH: 19
<212> TYPE: DNA
<213> ORGANISM: Homo sapiens

<400> SEQUENCE: 8
gcacggtaaa ccccaatta                                              19

<210> SEQ ID NO 9
<211> LENGTH: 20
<212> TYPE: DNA
<213> ORGANISM: Homo sapiens

<400> SEQUENCE: 9
ggcaacttgt ggtcttttt                                              20

<210> SEQ ID NO 10
<211> LENGTH: 25
<212> TYPE: DNA
<213> ORGANISM: Homo sapiens

<400> SEQUENCE: 10
gcagccacag aacttaccac tccag                                       25

<210> SEQ ID NO 11
```

```
<211> LENGTH: 25
<212> TYPE: DNA
<213> ORGANISM: Homo sapiens

<400> SEQUENCE: 11
taaatgcctc tggaatgtgg gtgat                                           25

<210> SEQ ID NO 12
<211> LENGTH: 9
<212> TYPE: DNA
<213> ORGANISM: Homo sapiens
<220> FEATURE:
<221> NAME/KEY: misc_feature
<222> LOCATION: (1)...(1)
<223> OTHER INFORMATION: n = C or G
<220> FEATURE:
<221> NAME/KEY: misc_feature
<222> LOCATION: (7)...(7)
<223> OTHER INFORMATION: n = Purine
<220> FEATURE:
<221> NAME/KEY: misc_feature
<222> LOCATION: (9)...(9)
<223> OTHER INFORMATION: n = pyrimidine

<400> SEQUENCE: 12 nctttgntn                                                             9

<210> SEQ ID NO 13
<211> LENGTH: 10
<212> TYPE: DNA
<213> ORGANISM: Homo sapiens

<400> SEQUENCE: 13
gatcaaaggg                                                           10

<210> SEQ ID NO 14
<211> LENGTH: 9
<212> TYPE: DNA
<213> ORGANISM: Homo sapiens
<220> FEATURE:
<221> NAME/KEY: misc_feature
<222> LOCATION: (1)...(1)
<223> OTHER INFORMATION: n = Purine
<220> FEATURE:
<221> NAME/KEY: misc_feature
<222> LOCATION: (3)...(3)
<223> OTHER INFORMATION: n = Pyrimidine
<220> FEATURE:
<221> NAME/KEY: misc_feature
<222> LOCATION: (9)...(9)
<223> OTHER INFORMATION: n = C or G

<400> SEQUENCE: 14 nancaaagn                                                             9

<210> SEQ ID NO 15
<211> LENGTH: 90
<212> TYPE: DNA
<213> ORGANISM: Homo sapiens

<400> SEQUENCE: 15
cagctgaagc ttgcatgcct gcaggatcaa aggggtaag atcaaagggg gtaagatcaa      60
aggtctagag ggtatataat ggatccggta                                      90
```